(12) United States Patent
Fukuma et al.

(10) Patent No.: US 12,262,948 B2
(45) Date of Patent: Apr. 1, 2025

(54) MICROSCOPE AND FUNCTION EXPANSION UNIT

(71) Applicant: Topcon Corporation, Tokyo (JP)

(72) Inventors: Yasufumi Fukuma, Tokyo (JP); Kazuhiro Oomori, Tokyo (JP); Hisashi Tsukada, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 1160 days.

(21) Appl. No.: 16/642,066

(22) PCT Filed: Jul. 9, 2018

(86) PCT No.: PCT/JP2018/025924
§ 371 (c)(1),
(2) Date: Dec. 4, 2020

(87) PCT Pub. No.: WO2019/044180
PCT Pub. Date: Mar. 7, 2019

(65) Prior Publication Data
US 2021/0113081 A1     Apr. 22, 2021

(30) Foreign Application Priority Data
Aug. 30, 2017 (JP) .................. 2017-165187

(51) Int. Cl.
*A61B 3/10*     (2006.01)
*A61B 3/00*     (2006.01)
*A61B 3/13*     (2006.01)

(52) U.S. Cl.
CPC .............. *A61B 3/13* (2013.01); *A61B 3/0008* (2013.01); *A61B 3/102* (2013.01)

(58) Field of Classification Search
CPC ......... A61B 3/13; A61B 3/0008; A61B 3/102; A61B 3/135; A61B 3/132
See application file for complete search history.

(56) References Cited

U.S. PATENT DOCUMENTS 5,954,711 A      9/1999  Ozaki et al.
11,871,994 B2 *  1/2024  Fukuma ................ A61B 3/102
(Continued)

FOREIGN PATENT DOCUMENTS

CN    101677767 A      3/2010
DE    2014010350 A1    1/2016
(Continued)

OTHER PUBLICATIONS

International Search Report and Written Opinion issued in PCT/JP2018/025924, dated Aug. 21, 2018.
(Continued)

*Primary Examiner* — George G. King
*Assistant Examiner* — Anna Smith
(74) *Attorney, Agent, or Firm* — BakerHostetler

(57) ABSTRACT

The present disclosure provides a microscope including a first optical member configured to guide light from a light source in a first optical axis direction; a first reflecting member configured to guide the light guided in the first optical axis direction in a second optical axis direction substantially orthogonal to the first optical axis direction; a second optical member configured to relay the light guided in the second optical axis direction; a second reflecting member configured to guide the light relayed by the second optical member in a third optical axis direction substantially orthogonal to the second optical axis direction; and a function expansion objective lens disposed on the third optical axis direction and configured to radiate the light guided in the third optical axis direction onto a predetermined portion of the observation target.

6 Claims, 13 Drawing Sheets

(56) References Cited

U.S. PATENT DOCUMENTS

| | | | | |
|---|---|---|---|---|
| 2008/0018855 A1* | 1/2008 | Larichev | ............... | A61B 3/032 |
| | | | | 600/558 |
| 2010/0033676 A1 | 2/2010 | De Vries et al. | | |
| 2011/0001930 A1* | 1/2011 | Levecq | ............... | A61B 3/1015 |
| | | | | 606/4 |
| 2013/0063698 A1* | 3/2013 | Akiba | .................... | G06T 5/004 |
| | | | | 351/206 |
| 2016/0007848 A1 | 1/2016 | Filippatos et al. | | |
| 2016/0091702 A1* | 3/2016 | Hauger | ............... | G02B 21/361 |
| | | | | 348/79 |
| 2016/0278636 A1* | 9/2016 | Fukuma | ................. | A61B 3/132 |
| 2017/0167848 A1* | 6/2017 | Kobayashi | ......... | G01B 9/02058 |

FOREIGN PATENT DOCUMENTS

| | | |
|---|---|---|
| EP | 2965688 A1 | 1/2016 |
| JP | 7194645 A | 8/1995 |
| JP | 2010522055 A | 7/2010 |
| JP | 201712430 A | 1/2017 |
| WO | 2008115060 A1 | 9/2008 |
| WO | 2017002379 A1 | 1/2017 |

OTHER PUBLICATIONS

International Preliminary Report on Patentability and Written Opinion issued in PCT/JP2018/025924, dated Mar. 12, 2020.

* cited by examiner

MICROSCOPE AND FUNCTION EXPANSION UNIT

The present U.S. Patent Application is a U.S. National Phase Application under 35 U.S.C. 371 of International Application PCT/JP2018/025924 filed on Jul. 9, 2018, which claims priority to Japanese Patent Application No. 2017-165187 filed on Aug. 30, 2017, the entire disclosures of which are incorporated herein by reference.

TECHNICAL FIELD

The present invention relates to a microscope including, in addition to an observation optical system for observing an observation target, a function expansion optical system for radiating light from a light source onto the observation target and acquiring, from the observation target, information other than information by the observation, or for applying a process by light to the observation target.

In particular, the present invention relates to a microscope equipped with an OCT apparatus (OCT: Optical Coherence Tomography) for acquiring a tomographic image of an observation target, the microscope being configured such that an optical path (OCT measurement light optical system) of measurement light, which includes a scanning function unit in an OCT optical system of the OCT apparatus, can be compactly assembled while being adapted to a primary function of the microscope.

The present invention relates to an ophthalmic microscope in which functions of, for example, a fundus camera, a slit lamp, an ophthalmic surgery microscope and the like are incorporated, and, relates, in particular, to an ophthalmic microscope to which an OCT measurement light optical system (an optical path of measurement light of an OCT apparatus including a two-dimensional scanning function unit) can be added as a function expansion unit.

BACKGROUND ART

A microscope is an apparatus which enlarges an observation target and enables observation by the naked eye by using an optical technology, and microscopes for various purposes of use have been developed. For example, an ophthalmic microscope is an apparatus for medical use or examination, which is capable of illuminating a patient's subject eye by an illumination optical system, and observing a subject eye by enlarging the subject eye by an observation optical system composed of a lens, etc. As such an ophthalmic microscope, there has been developed an ophthalmic microscope which is capable of acquiring a tomographic image of the subject eye by incorporating an OCT optical system in the primary configuration of the ophthalmic microscope.

OCT is a technology in which an interferometer is constituted by using a light source with low coherence (with a short coherence distance), and obtain a tomographic image of a biological tissue. Specifically, a light source with low coherence is used, and light from the light source is divided into two lights by a beam splitter. One light (measurement light) is radiated on the biological tissue and is reflected or scattered, and the other light (reference light) is reflected by a mirror. The measurement light is reflected or scattered at various depth positions of the biological tissue, and countless reflective lights or scattered lights are returned. When the measurement light returned to the beam splitter and the reflective light of the reference light are made confluent, only the reflective light or scattered light of the measurement light, which has traveled over the same distance as the reference light, interferes with the reflective light of the reference light and is detected.

Accordingly, the intensity of the measurement light reflected at various depths of the biological tissue can be detected by adjusting the positions of the beam splitter and the mirror and variously changing the path length of the reference light. By this OCT optical system, a tomographic image of the biological tissue can be acquired.

By providing the OCT optical system in the ophthalmic microscope, a tomographic image of the retina, cornea, iris or the like of the subject eye can be acquired, and not only a surface of a tissue but also a state of the inside of the tissue can be observed. Thereby, the precision of diagnosis of a disease of the eye can be enhanced, and the rate of success of ophthalmic surgery can be increased.

The OCT optical system used in the ophthalmic microscope is divided into an OCT measurement light optical system which is a path of measurement light traveling via the subject eye, and an OCT reference light optical system which is a path of reference light traveling not via the subject eye. In addition, the OCT measurement light optical system needs to be assembled in the ophthalmic microscope including an illumination optical system and an observation optical system in such a manner that measurement light can be made incident on the subject eye, and various methods have been developed.

For example, in a Galilean-type ophthalmic microscope including an observation optical system composed of a left-type observation optical system and a right-eye observation optical system of an observer and including one objective lens through which the optical axes of the left and right observation optical systems commonly pass, there is known a method in which light of an OCT light source, which is made incident from a lateral side of the objective lens, is reflected by a reflecting member immediately above the objective lens, is passed through the objective lens and is made incident on the subject eye (patent documents 1 and 2, etc.).

A description will be given of the above in greater detail. As illustrated in FIG. 13 (a drawing in which FIG. 1 of patent document 1 is cited), an ophthalmic microscope includes an observation optical system composed of lens groups 130, 140, 150, 170 and 180 including pairs of left and right lenses through which an optical axis of a left-eye observation optical system and an optical axis of a right-eye observation optical system are passed; one objective lens 110 through which the optical axis of the left-eye observation optical system and the optical axis of the right-eye observation optical system commonly pass; an OCT optical system 200, 250, 450, 460, 470; and an illumination optical system 310, 320, 330. In the OCT optical system, output light from an OCT light source 200 travels through an optical fiber 250 and is emitted, and, after the direction of the output light is controlled by two scanning mirrors 450 and 460, the output light is combined with illumination light from an illumination optical system in a beam combiner 340, and the combined light is reflected by a beam splitter 120, passed through the objective lens 110 and made incident on a subject eye 1000.

In addition, in a Galilean-type ophthalmic microscope, there is known a method in which light of an OCT light source is emitted from above an objective lens, and the light is passed through the objective lens and made incident on a subject eye (patent document 3).

Furthermore, in a Galilean-type ophthalmic microscope, there is known a method in which an optical path of an OCT measurement light optical system is made confluent with an optical path of an observation optical system in a substantially coaxial manner, and light is passed through an objective lens and made incident on a subject eye (patent documents 4 and 5).

In each of the above methods, the optical axis of the observation optical system and the optical axis of the OCT measurement light optical system commonly pass through one objective lens.

PRIOR ART REFERENCES

Patent Documents

Patent Document 1: JP H8-66421 A
Patent Document 2: JP 2008-264488 A
Patent Document 3: JP 2008-268852 A
Patent Document 4: Jpn. PCT National Publication No. 2010-522055 (WO2008-115060)
Patent Document 5: JP 2008-264490 A

DISCLOSURE OF THE INVENTION

Problems to be Solved by the Invention

By assembling the OCT optical system in the ophthalmic microscope, a tomographic image of the retina, cornea, iris or the like of the eye can be acquired, and not only a surface of a tissue but also a state of the inside of the tissue can be observed. Thereby, the precision of diagnosis of a disease of the eye can be enhanced, and the rate of success of ophthalmic surgery can be increased.

In conventional Galilean-type ophthalmic microscopes, as disclosed in patent documents 1-5, etc., many methods have been developed in which the optical axis of the observation optical system and the optical axis of the OCT measurement light optical system commonly pass through one objective lens. However, since the observation optical system and the OCT measurement light optical system are not independent from each other, it is necessary to design the OCT measurement light optical system and the observation optical system in an integrated manner.

As described above, in the conventional microscopes, when another optical system is assembled in addition to the observation optical system in order to expand the function, it is necessary to design both optical systems in an integrated manner, and free function expansion is difficult.

Thus, in consideration of the situation of the conventional art, an object of the present invention is to provide a microscope including, in addition to an observation optical system for observing an observation target, a function expansion optical system for radiating light from a light source onto the observation target and acquiring, from the observation target, information other than information by the observation, or for applying a process by light to the observation target.

Another object of the invention is to provide a microscope equipped with an OCT apparatus for acquiring a tomographic image of an observation target, the microscope being configured such that an optical path (OCT measurement light optical system) of measurement light, which includes a scanning function unit of the OCT apparatus, can be compactly assembled while being adapted to a primary function of the microscope.

Still another object of the invention is to provide a microscope to which an OCT measurement light optical system (an optical path of measurement light of an OCT apparatus including a two-dimensional scanning function unit) can be added as a function expansion unit.

Means for Solving the Problems

In order to solve the problems, the inventors of the present application, as a result of tremendous research effort, have found the following and arrived at the present invention: when a function expansion optical system (a function for radiating light from a light source onto an observation target and acquiring, from the observation target, information other than information by observation, or a function for applying a process by light to the observation target), in addition to an observation optical system, is added to a microscope, the function expansion optical system can be compactly assembled while being adapted to a primary function of the microscope, by bending twice a light guide path orthogonally along an optical axis.

Specifically, the outline of the microscope of the present invention is as follows.

(1)
A microscope including, in addition to an observation optical system for observing an observation target, a function expansion optical system for radiating light from a light source onto the observation target and acquiring, from the observation target, information other than information by the observation, or for applying a process by light to the observation target,
the function expansion optical system including:
a first optical member configured to guide light from the light source in a first optical axis direction;
a first reflecting member configured to guide the light guided in the first optical axis direction in a second optical axis direction substantially orthogonal to the first optical axis direction;
a second optical member configured to relay the light guided in the second optical axis direction;
a second reflecting member configured to guide the light relayed by the second optical member in a third optical axis direction substantially orthogonal to the second optical axis direction; and
a function expansion objective lens disposed on the third optical axis direction and configured to radiate the light guided in the third optical axis direction onto a predetermined portion of the observation target.

(2)
The microscope according to (1),
wherein an objective lens for the observation optical system has such a shape that a part of the objective lens is notched, and the function expansion objective lens is disposed in the notched part,
whereby an optical axis of the function expansion optical system does not pass through the objective lens through which an optical axis of the observation optical system passes.

(3)
The microscope according to (2),
wherein
the light source is an OCT light source,
the function expansion optical system is an OCT optical system including an OCT measurement light optical system constituting a reciprocal light guide path of measurement light from the OCT light source, and an OCT reference light optical system constituting a light guide path of reference light from the OCT light source, and the function expansion objective lens is an OCT objective lens.

(4)

The microscope according to (3), wherein the observation target is a subject eye, the microscope includes a front lens for switching an observation position of the subject eye, when the front lens is inserted on an optical path between the subject eye and the objective lens, the optical axis of the observation optical system and the optical axis of the OCT measurement light optical system pass through the front lens, in accordance with a focal distance of the front lens inserted on the optical path between the subject eye and the objective lens, a distance (1) and/or a distance (2) below automatically varies, 1) the distance between the objective lens and the front lens, and 2) the distance between the OCT objective lens and the front lens, and when the front lens is inserted and released on the optical path between the subject eye and the objective lens, a length of an optical path of the OCT reference light optical system automatically varies in accordance with the focal distance of the front lens.

(5)

The microscope according to (4), further including:

a lens discrimination mechanism configured to acquire information relating to the focal distance of the front lens that is inserted on the optical path between the subject eye and the objective lens;

a position adjusting mechanism configured to adjust a distance between the objective lens and the front lens and/or a distance between the OCT objective lens and the front lens; and a control mechanism configured to control the position adjusting mechanism, based on the information which relates to the focal distance of the front lens and is acquired by the lens discrimination mechanism.

(6)

The microscope according to any one of (1) to (5), wherein the function expansion optical system is incorporated as an expansion unit.

(7)

The microscope according to any one of (1) to (6), wherein when a microscope main body is viewed from a front side, an optical path along the first optical axis direction is formed from a rear toward a front at a slightly outward left or right position of the microscope main body, an optical path along the second optical axis direction is formed from an outside toward an inside of the microscope main body, and an optical path along the third optical axis direction is formed to extend through the function expansion objective lens from above downward in a center of the microscope main body.

(8)

A function expansion unit which adds, to a microscope main body including an observation optical system for observing an observation target, a function for acquiring, from the observation target, information other than information by the observation, or for applying a process by light to the observation target, the function expansion unit including:

a function expansion optical system, the function expansion optical system including:

a first optical member configured to guide light from a light source in a first optical axis direction;

a first reflecting member configured to guide the light guided in the first optical axis direction in a second optical axis direction substantially orthogonal to the first optical axis direction;

a second optical member configured to relay the light guided in the second optical axis direction;

a second reflecting member configured to guide the light relayed by the second optical member in a third optical axis direction substantially orthogonal to the second optical axis direction; and a function expansion objective lens disposed on the third optical axis direction and configured to radiate the light guided in the third optical axis direction onto a predetermined portion of the observation target.

(9)

The function expansion unit according to (8), further including:

a replacement objective lens for replacement of an objective lens of the observation optical system of the microscope main body, wherein the replacement objective lens has a partly notched shape, and the objective lens is replaced with the replacement objective lens, and the function expansion objective lens is disposed in the notched part of the replacement objective lens, whereby an optical axis of the function expansion optical system does not pass through the replacement objective lens through which an optical axis of the observation optical system passes.

(10)

The function expansion unit according to (9), wherein the light source is an OCT light source, the function expansion optical system is an OCT optical system including an OCT measurement light optical system, which constitutes a reciprocal light guide path of measurement light from the OCT light source and includes a scanning function unit configured to scan the measurement light from the OCT light source in a predetermined direction, and an OCT reference light optical system constituting a light guide path of reference light from the OCT light source, and the function expansion objective lens is an OCT objective lens.

(11)

The function expansion unit according to (10), wherein the observation target is a subject eye, the microscope main body or the function expansion unit includes a front lens for switching an observation position of the subject eye, when the front lens is inserted on an optical path between the subject eye and the replacement objective lens, the optical axis of the observation optical system and the optical axis of the OCT optical system pass through the front lens, in accordance with a focal distance of the front lens inserted on the optical path between the subject eye and the replacement objective lens, a distance (1) and/or a distance (2) below automatically varies,
1) the distance between the replacement objective lens and the front lens, and
2) the distance between the OCT objective lens and the front lens, and
when the front lens is inserted and released on the optical path between the subject eye and the replacement objective lens, a length of an optical path of the OCT reference light optical system automatically varies in accordance with the focal distance of the front lens.

(12)

The function expansion unit according to (11), further including:
a lens discrimination mechanism configured to acquire information relating to the focal distance of the front lens that is inserted on the optical path between the subject eye and the replacement objective lens;
a position adjusting mechanism configured to adjust a distance between the replacement objective lens and the front lens and/or a distance between the OCT objective lens and the front lens; and
a control mechanism configured to control the position adjusting mechanism, based on the information which relates to the focal distance of the front lens and is acquired by the lens discrimination mechanism.

(13)

The function expansion unit according to any one of (8) to (12),
wherein,
when the function expansion unit is attached to the microscope main body and the microscope main body is viewed from a front side,
an optical path along the first optical axis direction is formed from a rear toward a front at a slightly outward left or right position of the microscope main body,
an optical path along the second optical axis direction is formed from an outside toward an inside of the microscope main body, and
an optical path along the third optical axis direction is formed to extend through the function expansion objective lens from above downward in a center of the microscope main body.

Effect of the Invention

In the present invention, it is possible to provide a microscope including a function expansion optical system for acquiring information other than information by observation from an observation target, or for applying a process by light to the observation target.

In the present invention, when a function expansion optical system is added to a microscope, the function expansion optical system can be compactly assembled while being adapted to a primary function of the microscope, by bending twice a light guide path substantially orthogonally along an optical axis.

BRIEF DESCRIPTION OF THE DRAWINGS

FIG. 8(A) illustrates a case in which a lens having a power (refracting power) of D is inserted on the optical path as the front lens, and FIG. 8(B) illustrates a case in which a front lens having a power (refracting power) of D', which is greater than D, is inserted on the optical path.

FIG. 11(A) illustrates a case in which an anterior ocular segment, such as the cornea or iris, is observed without inserting the front lens between the objective lens and the subject eye, and FIG. 11(B) illustrates a case in which a posterior ocular segment, such as the retina of the fundus oculi, is observed by inserting the front lens between the objective lens and the subject eye.

DESCRIPTION OF EMBODIMENTS

Figure 1:
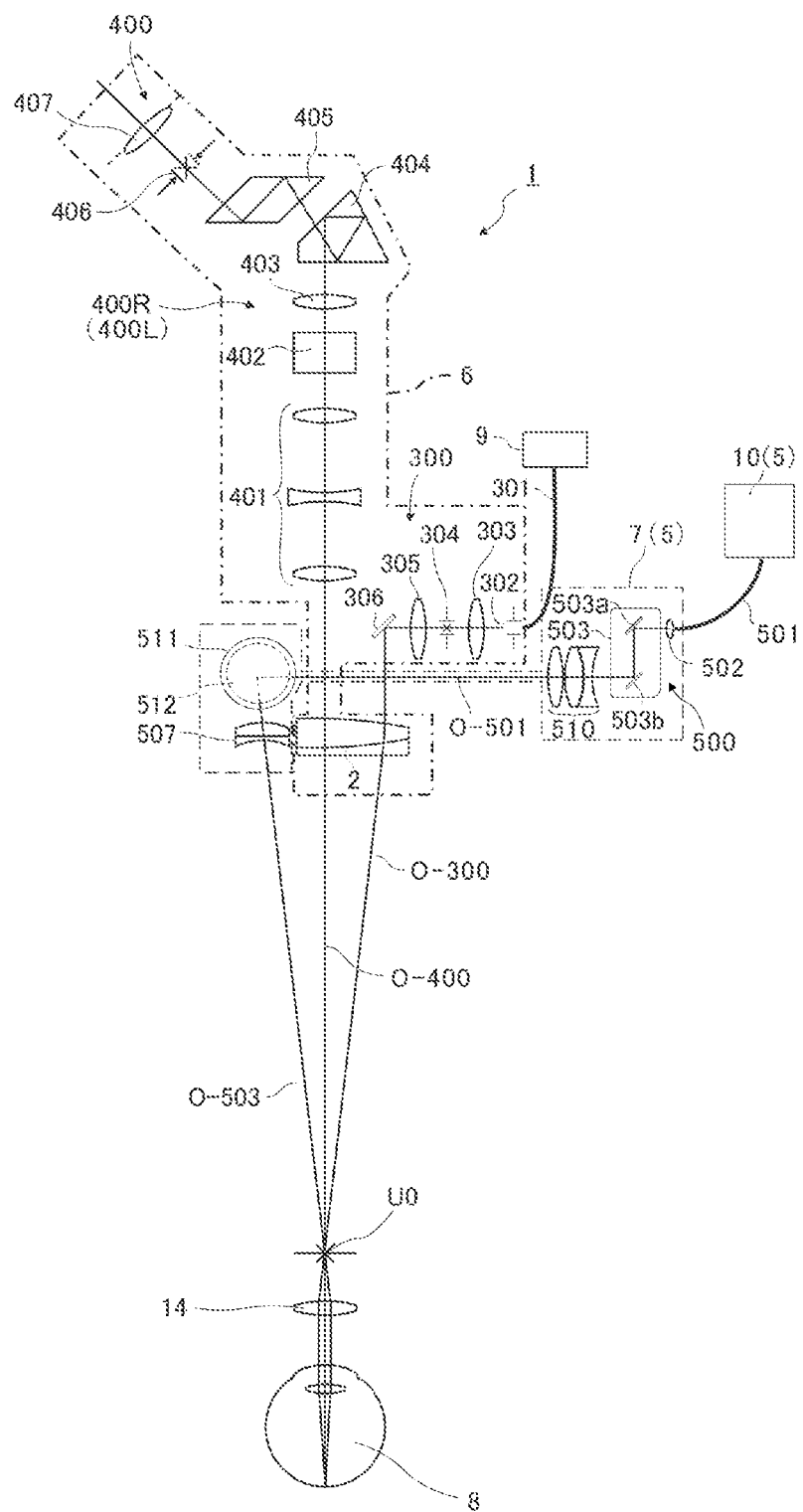
FIG. 1 is a schematic side view of a microscope of a first embodiment of the present invention.

1. Outline of Microscope of the Present Invention

The microscope of the present invention relates to a microscope including, in addition to an observation optical system for observing an observation target, a function expansion optical system for radiating light from a light source onto the observation target and acquiring, from the observation target, information other than information by the observation, or for applying a process by light to the observation target.

In the present invention, the "microscope" refers to an apparatus which includes an observation optical system and enables observation of an observation target by enlarging the observation target.

The "observation optical system" is configured to include optical elements such as a lens, a prism, etc., which enable observation of a subject eye by return light which is reflected/scattered from the subject eye that is illuminated. In the present invention, the "observation optical system" may include a left-eye observation optical system and a right-eye observation optical system, and, when parallax is caused in images acquired by the left and right observation optical systems, stereoscopic observation can be performed by binocular vision.

In addition, the "observation optical system" of the present invention may be an observation optical system which can observe a subject eye by an observer's naked eyes through eyepieces, ocular lenses or the like, or may be an observation optical system which receives reflective light or the like from the observation target by an imaging device (CCD) or the like and can cause a display to display the received reflective light or the like, or may be an observation optical system including both functions.

A function expansion optical system, which the microscope of the present invention includes, includes:
- a first optical member configured to guide light from a light source in a first optical axis direction;
- a first reflecting member configured to guide the light guided in the first optical axis direction in a second optical axis direction substantially orthogonal to the first optical axis direction;
- a second optical member configured to relay the light guided in the second optical axis direction;
- a second reflecting member configured to guide the light relayed by the second optical member in a third optical axis direction substantially orthogonal to the second optical axis direction; and
- a function expansion objective lens disposed on the third optical axis direction and configured to radiate the light guided in the third optical axis direction onto a predetermined portion of the observation target.

By the above optical configuration, the function expansion optical system can be compactly assembled in the microscope main body by bending twice the light guide path of the function expansion optical system substantially orthogonally along the optical axis. In addition, the function expansion optical system can be detachably attached to the microscope main body as a function expansion unit.

The words "substantially orthogonal" means that an angle between two optical axes is 80 to 100°. As the angle between two optical axes is closer to 90° (orthogonal), the occurrence of a phase difference due to reflection can be more surely prevented, and it is thus preferable that the two axes are crossed at an angle of 85 to 95°.

The observation optical system includes an objective lens as a lens disposed on an observation target side. The objective lens for the observation optical system may have such a shape that a part of the objective lens is notched, and a function expansion objective lens may be disposed in the notched part. Thereby, such an optical configuration can be made that the optical axis of a function expansion optical system does not pass through the objective lens through which the optical axis of the observation optical system passes.

By adopting this optical configuration, the observation optical system and the function expansion optical system can be configured to be independent from each other, and optical design can be made without mutual influence between the observation optical system and the function expansion optical system. Therefore, the advantageous effect that the degree of freedom of optical design is enhanced can be obtained.

Furthermore, since the observation optical system and the function expansion optical system are independent from each other, such optical design can easily be made that the function expansion optical system is separated from the observation optical system, and the function expansion optical system is detachably attached to the observation optical system.

As regards the notch in the objective lens, for example, the objective lens is notched by a cut surface. Typically, the objective lens is notched by a planar surface or a curved surface, which is parallel to, or crosses, the optical axis, as a cut surface.

In the microscope of the present invention, an OCT optical system can be adopted as the function expansion optical system. In this case, the light source of the function expansion optical system is an OCT light source, and the function expansion objective lens is an OCT objective lens.

The OCT optical system includes an OCT measurement light optical system and an OCT reference light optical system. The OCT measurement light optical system includes an optical element through which measurement light from the OCT light source travels, and constitutes a reciprocal light guide path of the measurement light. In addition, the OCT reference light optical system includes an optical element through which reference light from the OCT light source travels, and constitutes a light guide path of the reference light.

In the OCT measurement light optical system, a scanning function unit can be provided on the optical path of measurement light. The scanning function unit includes an XY scanning mechanism (two-dimensional scanning mechanism) and/or a Z scanning mechanism. These scanning mechanisms can be fabricated by, for example, MEMS (Micro Electro Mechanical Systems).

In the present invention, as optical elements used in the OCT optical system and observation optical system, use can be made of, for example, a lens, a prism, a mirror, an optical filter, a diaphragm, a diffraction grating, a polarizer element, and the like.

The microscope of the present invention can be configured as an ophthalmic microscope, an observation target of which is a subject eye. In addition, the ophthalmic microscope can also include an OCT optical system as a function expansion optical system.

When the microscope of the present invention is configured as an ophthalmic microscope, the ophthalmic microscope can further include a front lens (loupe) for switching an observation position of the subject eye.

The front lens is a lens which, when used, is temporarily inserted between the objective lens and the subject eye, and does not correspond to the "objective lens" in the present invention.

In the case where the microscope of the present invention includes the OCT optical system and the front lens, when the front lens is inserted on the optical path between the subject eye and the objective lens, the optical axis of the observation optical system and the optical axis of the OCT optical system pass through the front lens, and, therefore, an observation focal plane position or an OCT scanning plane position varies in accordance with a focal distance (power) of the front lens.

Thus, it is preferable to automatically vary the distance of the following (1) or (2) in accordance with the focal distance of the front lens that is inserted on the optical path between the subject eye and the objective lens.
1) Distance between the objective lens and the front lens, or
2) Distance between the OCT objective lens and the front lens.

By automatically varying the distance in this manner, in the microscope of the present invention, time-consuming manual adjustment for making the OCT scanning plane position or observation focal plane position accord with the observation target can be reduced.

Here, in order to vary the distance between the objective lens and front lens, both of, or either of, the objective lens and front lens may be moved relative to the microscope main body. In addition, in order to vary the distance between the OCT objective lens and front lens, both of, or either of, the OCT objective lens and front lens may be moved relative to the microscope main body. Preferably, by moving the front lens relative to the microscope main body, both the distance to the objective lens and the distance to the OCT objective lens can be varied.

In addition, in the microscope of the present invention, when the front lens is inserted or released on the optical path between the subject eye and the objective lens, the optical path length of measurement light of the OCT measurement light optical system varies, and a difference from the optical path length of reference light of the OCT reference light optical system varies, and, consequently, interference cannot correctly be caused to occur.

Thus, in the microscope of the present invention, when the front lens is inserted or released on the optical path between the subject eye and objective lens, it is preferable that the length of the optical path of reference light of the OCT optical system is automatically varied in accordance with the focal distance of the front lens.

By automatically varying the distance in this manner, a tomographic image by OCT can correctly be acquired in the microscope of the present invention.

The wording "the front lens is inserted or released" in this context includes not only a meaning that one kind of front lens is inserted or released on the optical path between the subject eye and the objective lens, but also a meaning that the front lens on the optical path is replaced with another kind of front lens.

In order to vary the length of the optical path of reference light of the OCT reference light optical system, an optical element can be used. For example, although not limited to the following, a mirror provided at a return point of the optical path of reference light may be moved and thereby the optical path length can be varied, and an optical path length correction member may be inserted or released on the optical path of reference light and the optical path length can be varied in accordance with a difference in refractive index between this member and the atmosphere.

In the present invention, the wording "automatically vary" means that the distance of (1) or (2), or the length of the optical path of reference light of the OCT reference light optical system, is varied not by a manual operation but by a mechanical and/or electrical mechanism.

2. First Embodiment

Hereinafter, an example of a microscope according to an embodiment of the present invention will be described with reference to the accompanying drawings.

Figure 2:
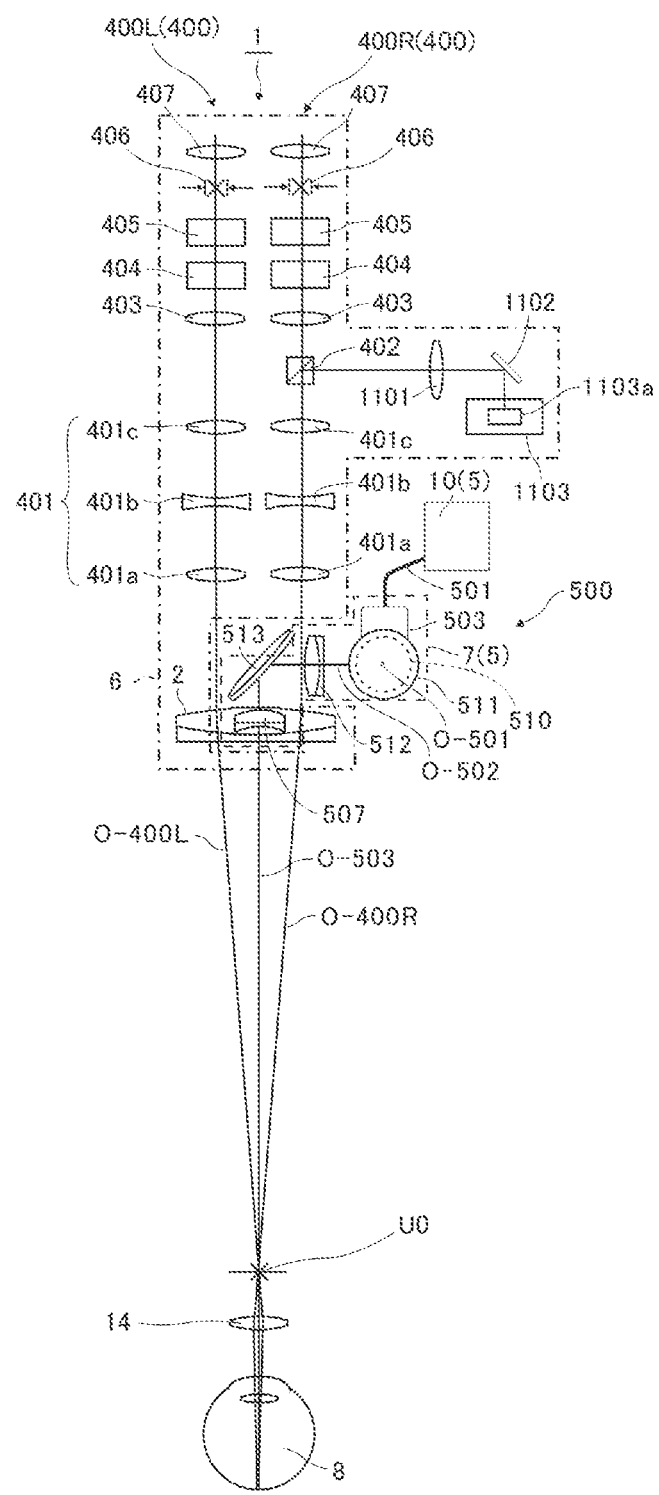
FIG. 2 is a schematic front view of the microscope of the first embodiment of the present invention.

FIG. 1 is a schematic side view of a microscope 1, and FIG. 2 is a schematic front view of the microscope 1.

As illustrated in FIG. 1 and FIG. 2, the microscope 1 is equipped with an OCT apparatus 5.

The microscope 1 includes an illumination optical system 300 (not illustrated in FIG. 2), an observation optical system 400 and an OCT measurement light optical system 500.

The observation optical system 400 can observe a predetermined portion of an observation target (the subject eye 8 in FIG. 1 and FIG. 2). As referred to in FIG. 1, the illumination optical system 300 can illuminate that part of the subject eye 8, which is to be observed.

As will be described later, the OCT apparatus 5, with which the microscope 1 is equipped, can acquire a tomographic image of the subject eye 8. The OCT measurement light optical system 500 is assembled in the microscope 1 as a part of the OCT apparatus 5. A reciprocal light guide path of measurement light is composed of the OCT measurement light optical system 500, the front lens 14 and a reflection surface (the cornea, retina, or the like) of the subject eye 8.

As explicitly illustrated in FIG. 2, the observation optical system 400 includes a right-eye observation optical system 400R and a left-eye observation optical system 400L. Note that FIG. 1 illustrates an entire configuration with respect to the right-eye observation optical system 400R, and illustrates only an objective lens 2 that is shared with the right-eye observation optical system 400R with respect to the left-eye observation optical system 400L.

In addition, as explicitly illustrated in FIG. 2, an optical axis O-400R of the right-eye observation optical system 400R and an optical axis O-400L of the left-eye observation optical system 400L pass through the objective lens 2.

In the present embodiment, the illumination optical system 300 and the observation optical system 400 are accommodated in a microscope main body 6. Besides, the OCT measurement light optical system 500 is accommodated in an OCT function expansion unit 7. In FIG. 1, the microscope main body 6 is indicated by a dot-and-dash line, and the OCT function expansion unit 7 is indicated by a broken line.

The OCT function expansion unit 7 is detachably coupled to the microscope main body 6 by a joint unit that is not illustrated.

The illumination optical system 300 illustrated in FIG. 1 is configured to include an illumination light source 9, an optical fiber 301, an emission light diaphragm 302, a condenser lens 303, an illumination field diaphragm 304, a collimate lens 305 and a reflection mirror 306. An optical axis of the illumination optical system 300 is indicated by O-300.

As illustrated in FIG. 1, the illumination light source 9 is provided outside the microscope main body 6 in the present embodiment. One end of the optical fiber 301 is connected to the illumination light source 9. The other end of the optical fiber 301 is disposed in such a position of the microscope main body 6 as to face the emission light diaphragm 302. Illumination light emitted from the illumination light source 9 is guided by the optical fiber 301, and is made incident on the condenser lens 303 via the emission light diaphragm 302.

The emission light diaphragm 302 functions to shut off a partial area of an emission aperture of the optical fiber 301. When the shut-off area by the emission light diaphragm 302 is varied, the emission area of illumination light is varied. Thereby, a radiation angle by illumination light, i.e. an angle between an incidence direction of illumination light to the subject eye 8 and the optical axis of the objective lens 2, can be changed.

The illumination field diaphragm 304 is provided at an optically conjugate position (a position of ×) with a front-side focal point position U0 of the objective lens 2. The collimate lens 305 converts the illumination light, which has passed through the illumination field diaphragm 304, to a parallel beam. The reflection mirror 306 reflects the illumination light, which is converted to the parallel beam by the collimate lens 305, toward the objective lens 2. The light reflected by the reflection mirror 306 passes through the objective lens 2 and is radiated on the subject eye 8.

The illumination light radiated on the subject eye 8 is reflected/scattered by a tissue of the subject eye, such as the cornea or retina. The reflected/scattered return light (also called "observation light") passes through the objective lens 2 and is incident on the observation optical system 400.

The observation optical system 400 is used in order to observe via the objective lens 2 the subject eye 8 which is illuminated by the illumination optical system 300.

As illustrated in FIG. 1 and FIG. 2, the observation optical system 400 is configured to include a variable power lens system 401, a beam splitter 402 (a beam splitter for acquiring image information for TV camera display), an imaging lens 403, an image erecting prism 404, an interpupillary distance adjusting prism 405, a view field diaphragm 406, and an ocular lens 407. An optical axis of the observation optical system 400 is indicated by O-400.

As illustrated in FIG. 1 and FIG. 2, the OCT apparatus 5 is composed of an OCT main body unit 10 and the OCT function expansion unit 7.

The OCT measurement light optical system 500 is accommodated in the OCT function expansion unit 7.

Figure 3:
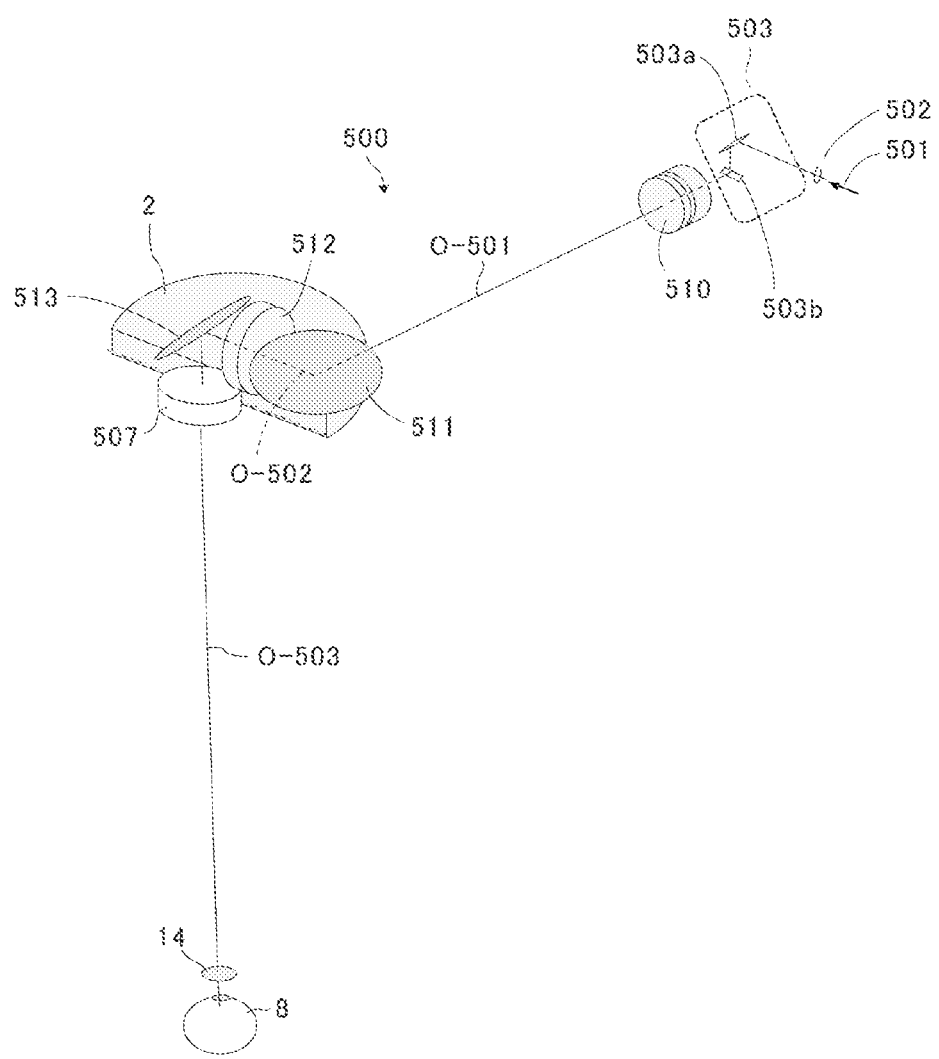
FIG. 3 is a perspective view of an OCT measurement light optical system in the microscope of the first embodiment of the present invention.
Figure 4:
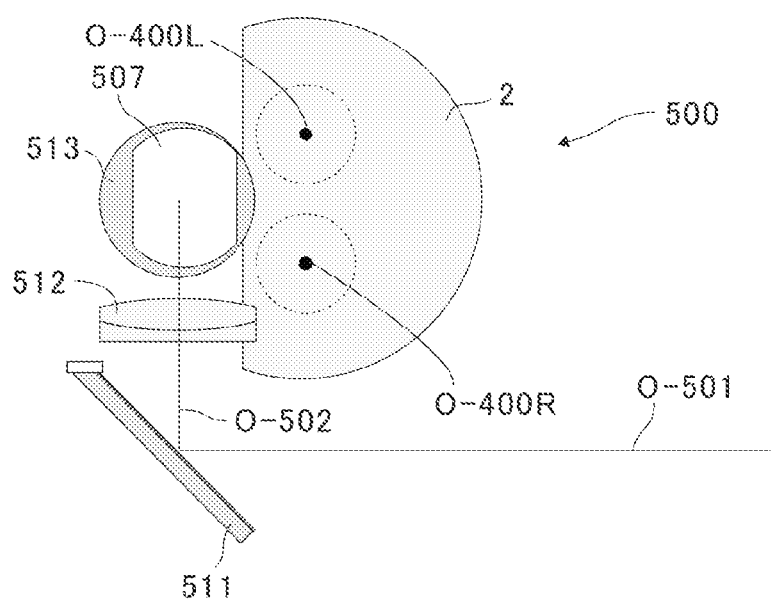
FIG. 4 is a plan view of the OCT measurement light optical system illustrated in FIG. 3.
Figure 5:
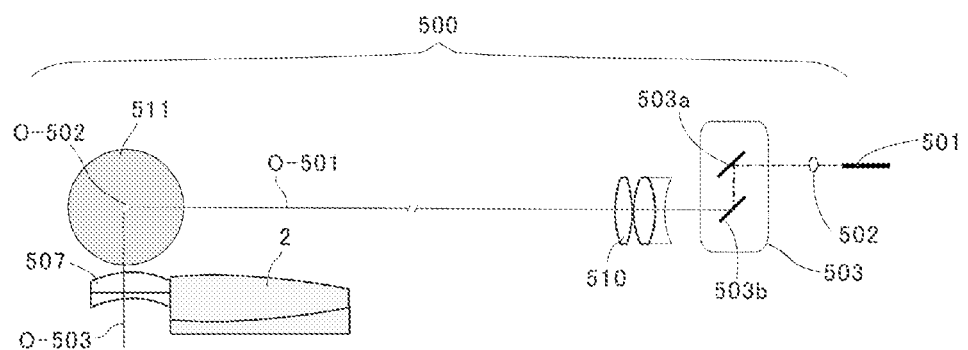
FIG. 5 is a side view of the OCT measurement light optical system illustrated in FIG. 3.
Figure 6:
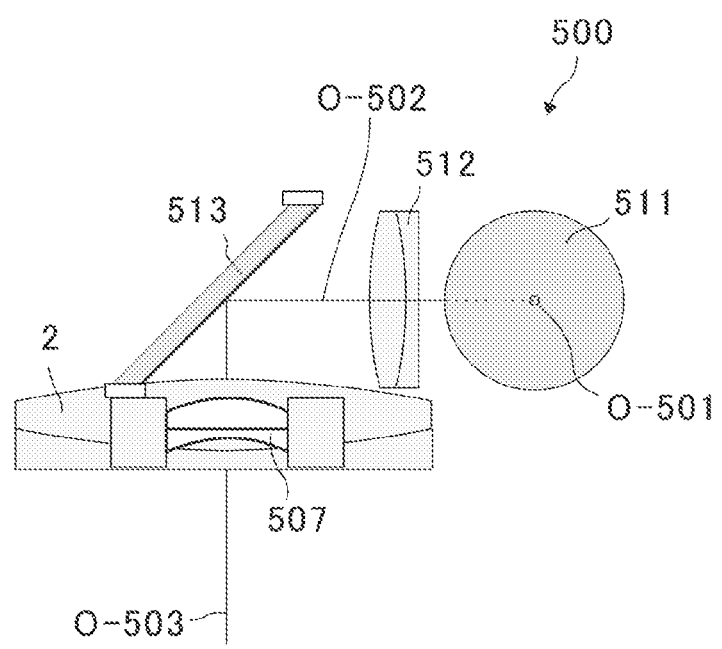
FIG. 6 is a front view of the OCT measurement light optical system illustrated in FIG. 3.

FIG. 3 is a perspective view of the OCT measurement light optical system 500, FIG. 4 is a plan view of the same, FIG. 5 is a side view of the same, and FIG. 6 is a front view of the same. Note that in FIG. 4 and FIG. 6, a collimate lens 502, a scanning function unit 503 and a first optical member 510 (to be described later) are not illustrated.

In FIG. 3 and FIG. 5, the OCT measurement light optical system 500 is configured to include a collimate lens 502, a scanning function unit 503, a first optical member 510, a first reflecting member 511, a second optical member 512, a second reflecting member 513, and a function expansion objective lens 507.

The scanning function unit 503 is a two-dimensional scanning mechanism including galvano mirrors 503a and 503b. The scanning function unit 503 is provided on a rear side (a side farther from the observer) of the microscope main body 6.

The first optical member 510 is an OCT imaging lens, and guides light, which is scanned by the scanning function unit 503, in a direction of a first optical axis O-501. When the microscope main body 6 is viewed from the front side, the first optical axis O-501 is formed from the depth side to the front side at a slightly outward position on the right side of the microscope main body 6, and the light scanned by the scanning function unit 503 is guided from the depth side toward the front side along the first optical axis O-501.

As illustrated in FIG. 3, FIG. 4, FIG. 5 and FIG. 6, the light guided along the first optical axis O-501 is guided by the first reflecting member 511 in a direction of a second optical axis O-502 which is orthogonal to the direction of the first optical axis O-501.

In the present embodiment, as referred to in FIG. 2, the second optical axis O-502 is formed from the rightward outside of the microscope main body 6 toward the inside.

The second optical member 512 is disposed on the second optical axis O-502, and light, which has passed through the second optical member 512, is reflected downward (in a direction substantially orthogonal to the second optical axis O-502) by the second reflecting member 513. This reflection optical path is indicated by a third optical axis direction O-503.

In the present embodiment, as illustrated in FIG. 1, the objective lens 2 is notched in a manner to have a cut surface which is substantially parallel to the optical axis O-400.

In the present embodiment, in this notched part, the function expansion objective lens 507 is accommodated.

The light guided by the third optical axis direction O-503 is focused at a predetermined position on the subject eye 8 side by the function expansion objective lens 507.

Note that in FIG. 1 and FIG. 2, the front-side focal point position U0 of the objective lens 2 exists in front of the subject eye 8, and the front lens 14 is disposed between the subject eye 8 and the front-side focal point position U0.

The front lens 14 is a lens which is used when the retina of the fundus oculi is observed, and the front lens 14 is inserted on the optical axes O-300, O-400L, O-400R and O-503 in front of the subject eye by moving means that is not illustrated. In this case, the front-side focal point position U0 of the objective lens 2 is conjugate with the retina of the fundus oculi. In addition, when the anterior ocular segment, such as the cornea, iris or the like, is observed, observation is performed by releasing the front lens 14 from the front side of the subject eye 8.

As described above, the optical axis O-500 of the OCT measurement light optical system 500 extends through the function expansion objective lens 507, and the optical axis O-500 of the OCT measurement light optical system 500 is separated from the optical axis O-400 of the observation optical system 400.

Accordingly, the OCT measurement light optical system 500 and the observation optical system 400 are independent from each other.

In the present invention, the function expansion optical system is not limited to the OCT measurement light optical system, and use can be made of an optical system for acquiring information from an observation target by radiating light on the observation target, or for applying a process to the observation target. Although not limited to the following, for example, an SLO optical system, a photocoagulation treatment laser optical system, or the like can be used as the optical system.

The SLO optical system is an optical system which constitutes a scanning laser ophthalmoscope, and is an optical system for radiating a laser beam into the eyeball by scanning the laser beam, receiving reflective light by a photodetection element, and forming an image by the reflective light. Normally, the SLO optical system includes an optical scanning function unit which scans light that is output from an SLO light source, and can radiate a laser beam on a subject eye via the first optical member, first reflecting member, second optical member, second reflecting member and function expansion objective lens of the present invention. In addition, a laser beam reflected by the subject eye is made to travel through the same path in an opposite direction, and is detected by a reflective light detector including a photodetection element, and a detected signal can be made into an image by an image generation unit.

The photocoagulation treatment laser optical system is an optical system for use in a laser coagulation treatment which suppresses the progression of an ophthalmic disease by radiating a laser beam of a specific wavelength onto a lesion tissue in the retina or the like. Normally, the photocoagulation treatment laser optical system can switchably guide a laser beam which is output from a laser light source for treatment, and a laser beam which is output from a laser light source for sighting, through an identical optical path, and can radiate the laser beam on the subject eye via the first optical member, first reflecting member, second optical member, second reflecting member and function expansion objective lens of the present invention. In a laser coagulation treatment, a lesion part of the subject eye is sighted by the laser for sighting, and then the laser for sighting is switched to the laser for treatment, and thereby a treatment laser beam can exactly be radiated on the lesion part.

As illustrated in FIG. 2, the beam splitter 402 of the right-eye observation optical system 400R separates part of the observation light, which is guided from the subject eye 8 along the right-eye observation optical system, and guides the separated part to a photographing optical system 1100. The photographing optical system 1100 is configured to include an imaging lens 1101, a reflection mirror 1102, and a TV camera 1103. Image information which the TV camera 1103 acquires is sent to a monitor that is not illustrated, and is displayed on the monitor.

As illustrated in FIG. 1 and FIG. 2, the image erecting prism 404 converts an inverted image to an erected image. The interpupillary distance adjusting prism 405 is an optical element for adjusting a distance between left and right observation optical paths in accordance with an observer's interpupillary distance (a distance between the left eye and the right eye). The view field diaphragm 406 restricts the observer's view field by shutting off a peripheral area in a cross section of observation light. The view field diaphragm 406 is provided at a conjugate position (a position of x) with the front-side focal point position U0 of the objective lens 2.

The right-eye observation optical system 400R and left-eye observation optical system 400L may be configured to include a stereovariator which is configured to be insertable/releasable in/from the optical path. The stereovariator is an optical axis position changing element for changing a relative position between the optical axes O-400L and O-400R of the left and right observation optical systems, which are guided by the left and right variable power lens systems 401. The stereovariator is evacuated, for example, to an evacuation position provided on the observer side with respect to the observation optical path.

Figure 7:
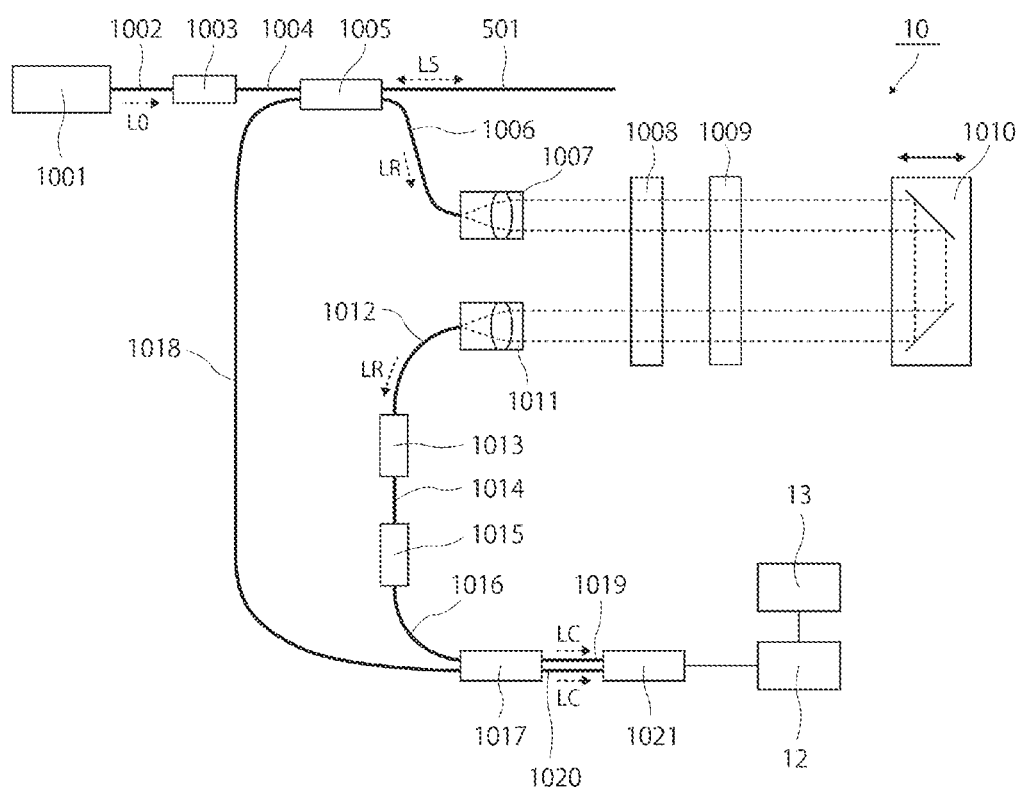
FIG. 7 is a view illustrating an optical configuration of an OCT apparatus for use in the microscope of the first embodiment of the present invention.

FIG. 7 is a drawing schematically illustrating an optical configuration of an OCT main body unit 10 for use in the microscope 1 of the present embodiment.

As illustrated in FIG. 7, the OCT main body unit 10 constitutes an interferometer which divides light L0 that is emitted from an OCT light source unit 1001 into measurement light LS and reference light LR, and which detects interference between the measurement light LS and reference light which travel through different optical paths.

The OCT light source unit 1001, like a general Swept Source type OCT apparatus, is configured to include a wavelength scanning type (wavelength sweep type) light source which can scan (sweep) the wavelength of emission light. The OCT light source unit 1001 temporally varies the output wavelength in a near-infrared wavelength which is not visually recognizable by the eyes of a human. Light emitted from the OCT light source unit 1001 is indicated by sign L0.

The light L0, which is output from the OCT light source unit 1001, is guided to a polarization controller 1003 by an optical fiber 1002, and the polarization state of the light L0 is adjusted. The polarization controller 1003 adjusts the polarization state of the light L0 that is guided through the optical fiber 1002, by applying stress from outside to the optical fiber 1002 which is formed, for example, in a loop shape.

The light L0, the polarization state of which was adjusted by the polarization controller 1003, is guided to a fiber coupler 1005 by an optical fiber 1004, and is divided into the measurement light LS and reference light LR.

As illustrated in FIG. 7, the reference light LR is guided to a collimator 1007 by an optical fiber 1006 and converted to a parallel beam. The reference light LR, which is converted to the parallel beam, travels through an optical path length correction member 1008 and a dispersion compensation member 1009, and is guided to a corner cube 1010. The optical path length correction member 1008 functions as delay means for making coincident the optical path lengths (optical distances) of the reference light LR and measurement light LS. The dispersion compensation member 1009 functions as dispersion compensation means for making coincident the dispersion characteristics of the reference light LR and measurement light LS.

The corner cube 1010 changes the direction of travel of the reference light LR, which is converted to the parallel beam by the collimator 1007, to an opposite direction. The optical path of the reference light LR, which is incident on the corner cube 1010, and the optical path of the reference light LR, which is emitted from the corner cube 1010, are parallel. In addition, the corner cube 1010 is configured to be movable in a direction along the incidence optical path and emission optical path of the reference light LR. By this movement, the length of the optical path (reference optical path) of the reference light LR is changed.

As illustrated in FIG. 7, the reference light LR, which has traveled via the corner cube 1010, travels through the dispersion compensation member 1009 and optical path length correction member 1008, is converted from the parallel beam to a convergent beam by a collimator 1011, made incident on an optical fiber 1012 and guided to a polarization controller 1013, and the polarization state of the reference light LR is adjusted.

The polarization controller 1013 has, for example, the same configuration as the polarization controller 1003. The reference light LR, the polarization state of which was adjusted by the polarization controller 1013, is guided to an attenuator 1015 by an optical fiber 1014, and the light amount is adjusted under the control of an arithmetic control unit 12. The reference light LR, the light amount of which was adjusted by the attenuator 1015, is guided to a fiber coupler 1017 by an optical fiber 1016.

As is understood from FIG. 1 and FIG. 7, the measurement light LS generated by the fiber coupler 1005 is guided to the collimate lens 502 by an optical fiber 501. As referred to in FIG. 1 and FIG. 2, the measurement light made incident on the collimate lens 502 is radiated on the subject eye 8 via the galvano mirrors 503a and 503b, first optical member 510, first reflecting member 511, second optical member 512, and second reflecting member 513. The measurement light is reflected/scattered at various depth positions of the subject eye 8. Backscattered light of the measurement light by the subject eye 8 travels through the same path as the forward path in an opposite direction, and, as illustrated in FIG. 7, is guided to the fiber coupler 1005 and arrives at the fiber coupler 1017 via an optical fiber 1018.

The fiber coupler 1017 generates interference light by compounding (causing interference between) the measurement light LS made incident via the optical fiber 1018 and the reference light (LR) made incident via the optical fiber 1016. The fiber coupler 1017 generates a pair of interference lights LC by branching the interference light of the measurement light LS and reference light LR at a predetermined branching ratio (e.g. 50:50). The pair of interference lights LC emitted from the fiber coupler 1017 are guided to a detector 1021 by two optical fibers 1019 and 1020, respectively.

The detector 1021 is, for example, a balanced photodiode (Balanced Photo Diode: hereinafter "BPD") which includes a pair of photodetectors that detect a pair of interference lights LC, respectively, and outputs a difference between detection results by the photodetectors. The detector 1021 sends a detection result (detection signal) to the arithmetic control unit 12. The arithmetic control unit 12 forms a tomographic image by applying a Fourier transform or the like to a spectrum distribution based on the detection result obtained by the detector 1021, for example, with respect to each of serial wavelength scans (with respect to each A line). The arithmetic control unit 12 causes a display unit 13 to display the formed image.

In the present embodiment, although a Michelson interferometer is adopted, an interferometer of a freely chosen type, for example, a Mach-Zehnder interferometer, may be applied.

Figure 8:
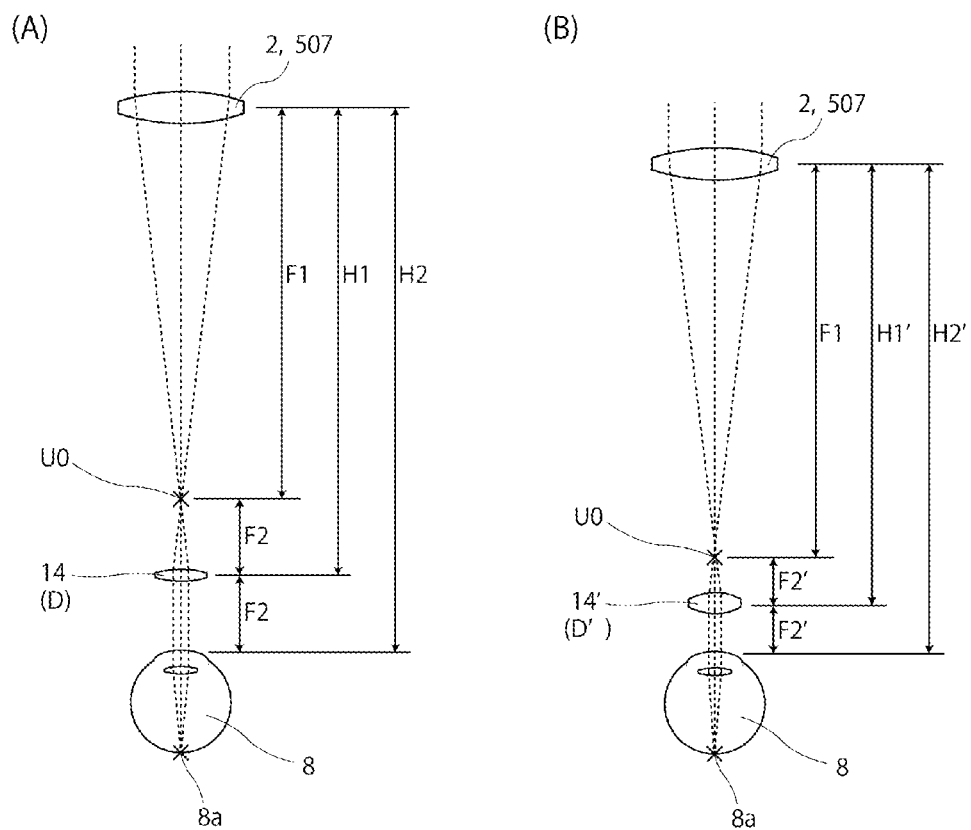
FIG. 8 is a drawing schematically illustrating a case in which a front lens is inserted on an optical path between a subject eye and an objective lens in the microscope of the first embodiment of the present invention.

FIG. 8 is a schematic view illustrating a case in which the front lens is inserted on the optical path between the subject eye and the objective lens in the microscope of the first embodiment of the present invention. As illustrated in FIG. 8, a focal distance of the objective lens 2 is F1, and a position at a distance of F1 from the objective lens is a front-side focal point position U0 of the objective lens. A light flux from the illumination optical system passes through the objective lens 2 and front lens 14, and illuminates the inside of the subject eye 8. Reflective light, which is reflected by the retina 8a in the subject eye, forms an image at a rear-side focal point position of the front lens 14. By making the rear-side focal point position of the front lens 14 agree with U0 that is the front-side focal point position of the objective lens 2, the focal point (observation focal plane) of the observation optical system is made to accord with the retina 8a and the retina can be observed in a focused state.

FIG. 8(A) illustrates a case in which a lens having a power (refracting power) of D is inserted on the optical path as the front lens 14, and FIG. 8(B) illustrates a case in which a front lens 14' having a power (refracting power) of D', which is greater than D, is inserted on the optical path. Since the focal distance of the front lens 14, 14' can be calculated from an inverse number of the power (refracting power) of the lens, a focal distance F2' of the front lens in FIG. 8(B) is shorter than a focal distance F2 of the front lens in FIG. 8(A). As is clear from the comparison between FIG. 8(A) and FIG. 8(B), it is necessary to make a distance H1, H1' between the objective lens 2 and front lens 14 longer in the case of FIG. 8(A) in which the front lens 14 with a long focal distance (low power) is used, than in the case of FIG. 8(B). It is also necessary to make a distance H2, H2' between the objective lens 2 and subject eye 8 longer in the case of FIG. 8(A) in which the front lens 14 with a long focal distance (low power) is used, than in the case of FIG. 8(B).

As is clear from the above comparison between FIG. 8(A) and FIG. 8(B), in order to make the focal point (observation focal plane) of the observation optical system accord with the retina, it is necessary to vary the distance between the objective lens and subject eye and to vary the distance between the objective lens and front lens, in accordance with the focal distance (power) of the front lens.

The same applies not only to the focal point of the observation optical system, but also to the focal point of the OCT optical system. Specifically, if the objective lens 2 in FIG. 8 is replaced with the OCT objective lens 507, the rear-side focal point position of the front lens 14 is made to agree with U0 that is the front-side focal point position of the OCT objective lens 507, and thereby the focal point (OCT scanning plane) of the OCT optical system is made to accord with the retina 8a, and the retina can be scanned in a focused state and a tomographic image can be acquired.

Here, as is clear from the comparison between FIG. 8(A) and FIG. 8(B), it is necessary to make a distance H1, H1' between the OCT objective lens 507 and front lens 14 longer in the case of FIG. 8(A) in which the front lens 14 with a long focal distance (low power) is used, than in the case of FIG. 8(B). It is also necessary to make a distance H2, H2' between the OCT objective lens 507 and subject eye 8 longer in the case of FIG. 8(A) in which the front lens 14 with a long focal distance (low power) is used, than in the case of FIG. 8(B).

Accordingly, in order to make the focal point (OCT scanning plane) of the OCT optical system accord with the retina, it is necessary to vary the distance between the OCT objective lens and subject eye and to vary the distance between the OCT objective lens and front lens, in accordance with the focal distance (power) of the front lens.

Figure 9:
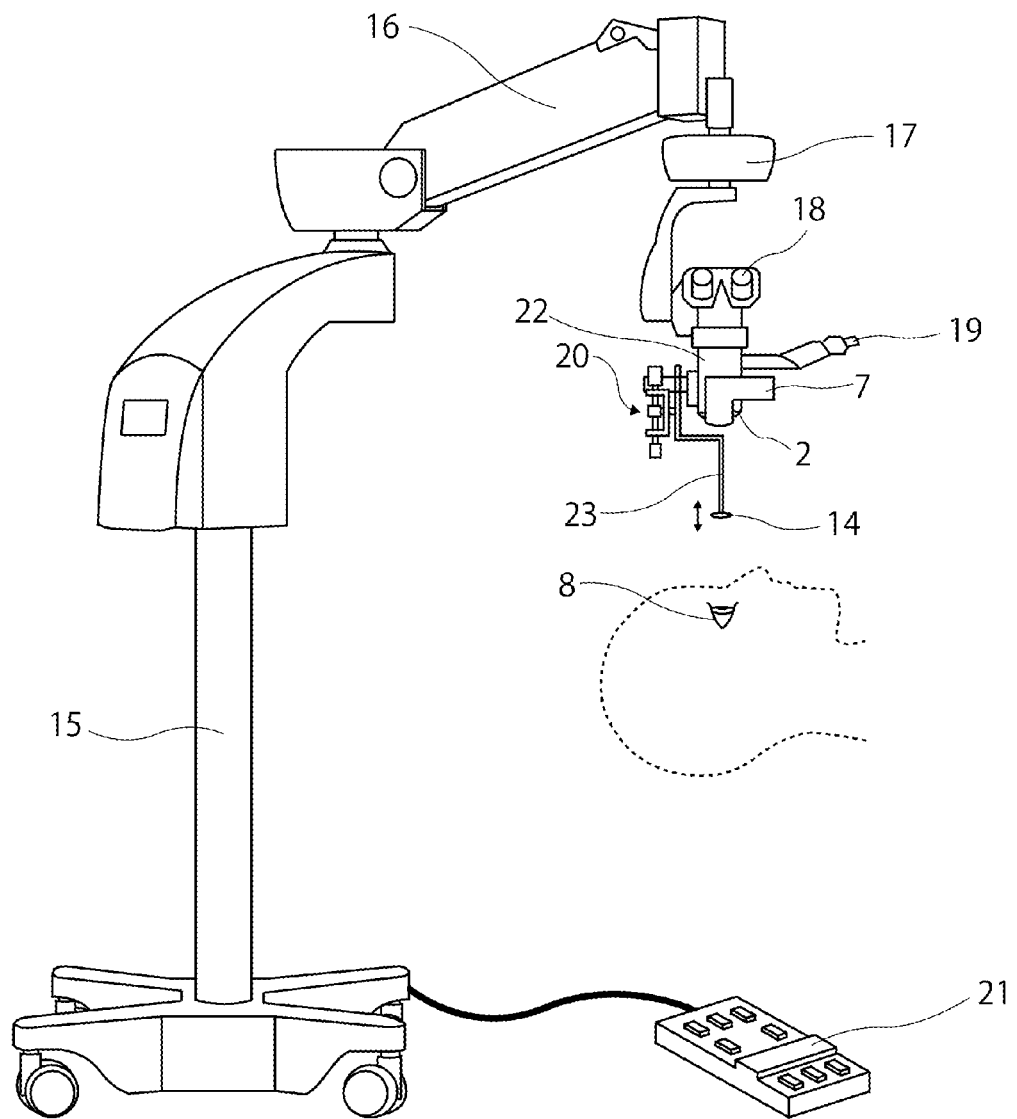
FIG. 9 is a drawing schematically illustrating the microscope of the first embodiment of the present invention and a positioning apparatus which holds the microscope.

The distance between the objective lens and the subject eye can be varied by holding the microscope by a positioning apparatus and vertically moving the microscope. FIG. 9 is a schematic view illustrating the microscope of the first embodiment of the present invention and a positioning apparatus which holds the microscope. As illustrated in FIG. 9, the positioning apparatus includes a support column 15, an arm 16, and an X-Y fine movement apparatus 17, and holds the microscope by these components. A three-dimensional position of the microscope, which is held by the positioning apparatus, can be moved manually or by an actuator provided in the inside of the positioning apparatus, and can be fixed by an electromagnetic lock or the like provided in the inside of the positioning apparatus in such a manner that the three-dimensional position of the microscope does not move. The actuator and the electromagnetic lock are controlled by a control unit of the microscope.

The microscope includes a surgeon microscope 18 which an ophthalmic surgeon, who performs a surgical operation of the subject eye 8, uses, and an assistant microscope 19 which a surgical operation assistant uses, and a surgical operation can be performed while both the surgeon and the surgical operation assistant are observing the subject eye. The three-dimensional position of the microscope can also be manipulated by a footswitch 21, and the surgeon can adjust the position of the microscope by an operation by the foot, while holding an operation instrument by both hands. The objective lens 2 is provided at a lower end of a lens-barrel 22 of the microscope. In addition, the front lens 14 can be inserted between the objective lens 2 and the subject eye 8 by a holding arm 23.

The distance between the objective lens 2 and subject eye 8 can be varied by vertically moving the microscope by the positioning apparatus.

Besides, as regards the OCT objective lens not illustrated, which is provided in a position further toward the front side than the objective lens 2 in FIG. 9, the distance between the OCT objective lens and the subject eye 8 can be varied by vertically moving the microscope by the positioning apparatus.

For example, when the front lens 14' is released from the state in which the front lens 14' with the power of D' illustrated in FIG. 8(B) is inserted on the optical path, and is replaced with the front lens 14 with the power of D illustrated in FIG. 8(A), the distance between the objective lens 2 and subject eye 8 may be changed from H2' to H2 by upwardly moving the microscope.

In this case, in accordance with the upward movement of the microscope, the front lens 14 moves upward by the same distance. Thus, the distance between the objective lens 2 and front lens 14 is kept at H1'. It is thus necessary to move the front lens 14 downward relative to the objective lens 2, and to set the distance between the objective lens 2 and front lens 14 at H1.

As illustrated in FIG. 9, the distance between the objective lens 2 and the front lens 14 can be varied by a front lens position adjusting mechanism 20.

Figure 10:
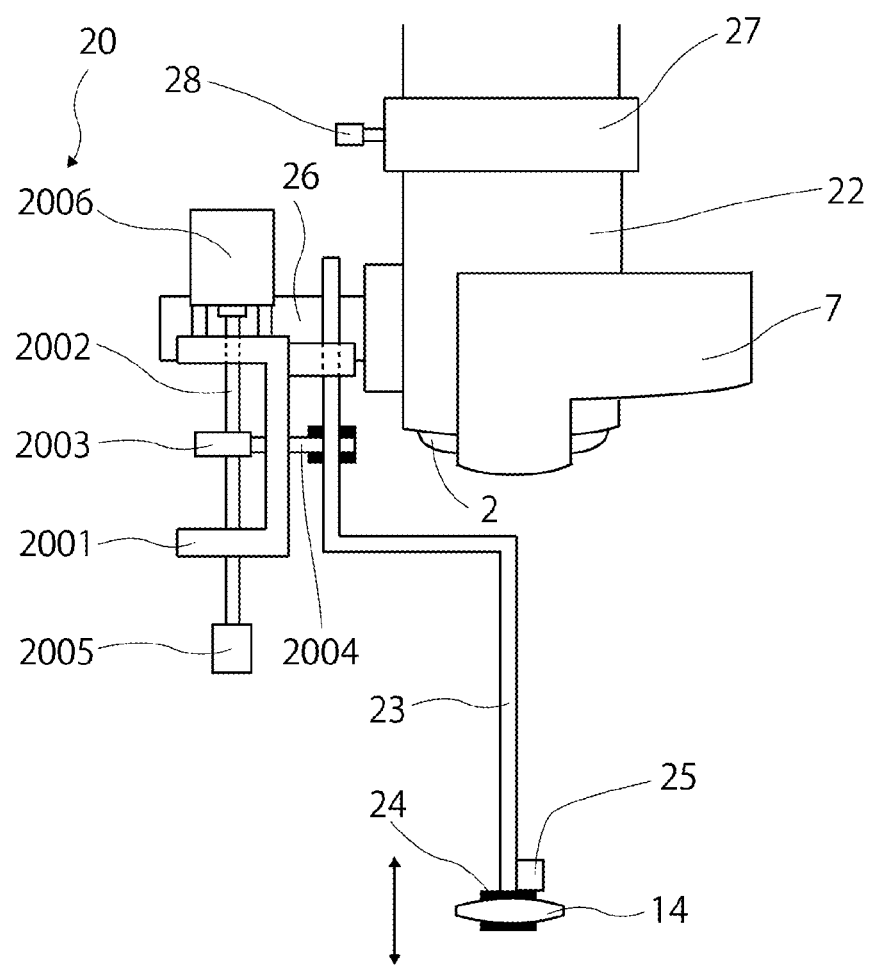
FIG. 10 is a drawing schematically illustrating a peripheral part of a front lens position adjusting mechanism of the microscope of the first embodiment of the present invention.

Referring to FIG. 10, the front lens position adjusting mechanism will be described below.

FIG. 10 is a schematic view illustrating a peripheral part of the front lens position adjusting mechanism in the microscope of the first embodiment of the present invention. As illustrated in FIG. 10, the objective lens 2 is provided at the lower end of the lens-barrel 22 of the microscope. In addition, the OCT function expansion unit 7 including therein the OCT measurement light optical system is attached to the lens-barrel 22, and the OCT objective lens (not illustrated) is provided at a lower end of the OCT function expansion unit 7. In addition, the front lens 14 can be inserted by the holding arm 23 on the optical path between the objective lens 2 and the subject eye. The front lens 14 can be attached/detached to/from a holding plate 24 provided at a tip end of the holding arm 23, and various kinds of front lenses 14 with different powers can be switchably used. A tag is attached to the front lens 14, and when the information of the tag is read by a tag detector 25 and sent to the control unit, they control unit can discriminate the kind of the front lens 14.

The control unit discriminates the kind of the front lens 14, and acquires information relating to the focal distance of the front lens 14 that is inserted on the optical path by referring to information of a storage medium which stores information relating to the focal distance corresponding to the kind of the front lens. Based on the acquired information, the control unit calculates the distance between the objective lens 2 and front lens 14 for setting a focal point at an observation target, and adjusting the position of the front lens 14 by controlling the front lens position adjusting mechanism 20.

As illustrated in FIG. 10, the front lens position adjusting mechanism 20 includes a support bracket 2001, and a rotation screw 2002 that vertically extends is fitted through a screw hole provided in the support bracket 2001. A movable plate 2003 is coupled to the rotation screw 2002, and the movable plate 2003 and holding arm 23 are coupled by a coupling arm 2004.

The rotation screw 2002 can be manually rotated by pinching a fine movement adjusting knob 2005, and thereby the movable plate 2003 can be vertically moved. In addition, in interlock with the vertical movement of the movable plate 2003, the front lens 14, which is coupled to the movable plate 2003 via the coupling arm 2004 and holding arm 23, can be vertically moved.

The rotation screw 2002 can also be rotated by a motor 2006, the rotation of which is controlled by the control unit. Thereby, the front lens 14 can be vertically moved by automatic control.

The control unit discriminates the kind of the front lens 14 and calculates, based on the focal distance (power) of the front lens 14, the distance between the objective lens 2 and front lens 14 for setting a focal point at the observation target. In addition, the control unit can automatically adjust the position of the front lens 14 by controlling the front lens position adjusting mechanism 20, such that the distance between the objective lens 2 and front lens 14 becomes equal to the calculated distance.

For example, when the front lens 14' with the power of D' illustrated in FIG. 8(B) is replaced with the front lens 14 with the power of D illustrated in FIG. 8(A), the control unit discriminates the kind of the front lens 14, controls the front lens position adjusting mechanism, and automatically changes the distance between the objective lens 2 and front lens 14 to H1.

Thereafter, using the positioning apparatus illustrated in FIG. 9, the surgeon or the surgical operation assistant moves the position of the microscope upward by a manual operation or by operating the footswitch 21 or the like. At this time, while performing microscope observation, the surgeon or surgical operation assistant moves the position of the microscope upward until the focus is set on the fundus oculi. Then, at the position where the focus is set, the distance between the objective lens 2 and the subject eye 8 is set to H2 illustrated in FIG. 8(A).

In this manner, after the distance between the objective lens and front lens is automatically changed, the microscope can be moved upward until the focus is set by microscope observation, and, besides, the focus can be set by automatic control. For example, the control unit of the microscope can calculate the distance H2 between the objective lens 2 and subject eye 8 illustrated in FIG. 8(A) for setting the focus on the observation target in accordance with the focal distance (power) of the front lens 14, can control the actuator of the positioning apparatus illustrated in FIG. 9, and can automatically move the microscope upward.

The distance between the OCT objective lens not illustrated, which is located further toward the front side than the objective lens 2 in FIG. 10, and the front lens 14 can also be automatically adjusted by the front lens position adjusting mechanism 20.

Specifically, the control unit discriminates the kind of the front lens 14 and calculates, based on the focal distance (power) of the front lens 14, the distance between the OCT objective lens 507 and front lens 14 for setting a focal point (OCT scanning plane) of the OCT optical system at the observation target. In addition, the control unit can automatically adjust the position of the front lens 14 by controlling the front lens position adjusting mechanism 20, such that the distance between the OCT objective lens 507 and front lens 14 becomes equal to the calculated distance.

As illustrated in FIG. 10, the holding arm 23 and the front lens position adjusting mechanism 20 are held by a fixing bracket 26 which is coupled to the lens-barrel 22. In addition, the holding arm 23 and the front lens position adjusting mechanism 20 are configured to be rotatable around the axis of the fixing bracket 26, and thereby the front lens 14 can be inserted and released on the optical path between the objective lens 2 and the subject eye.

If the front lens 14 is inserted on the optical path, the image of the subject eye is inverted into an inverted image, and thus a lens unit for restoring the inverted image to an erected image is provided in an inverter unit 27. For example, an optical system disclosed in Japanese Examined Patent Publication (Kokoku) No. H7-48091 can be used for the optical system of the lens unit provided in the inverter unit 27. The lens unit can be inserted and released on the optical path in the lens-barrel by a switching lever 28 by a manual operation in interlock with the insertion and release of the front lens, and also the lens unit can automatically be inserted and released on the optical path in the lens-barrel by operating the actuator in interlock with the insertion and release of the front lens.

Figure 11:
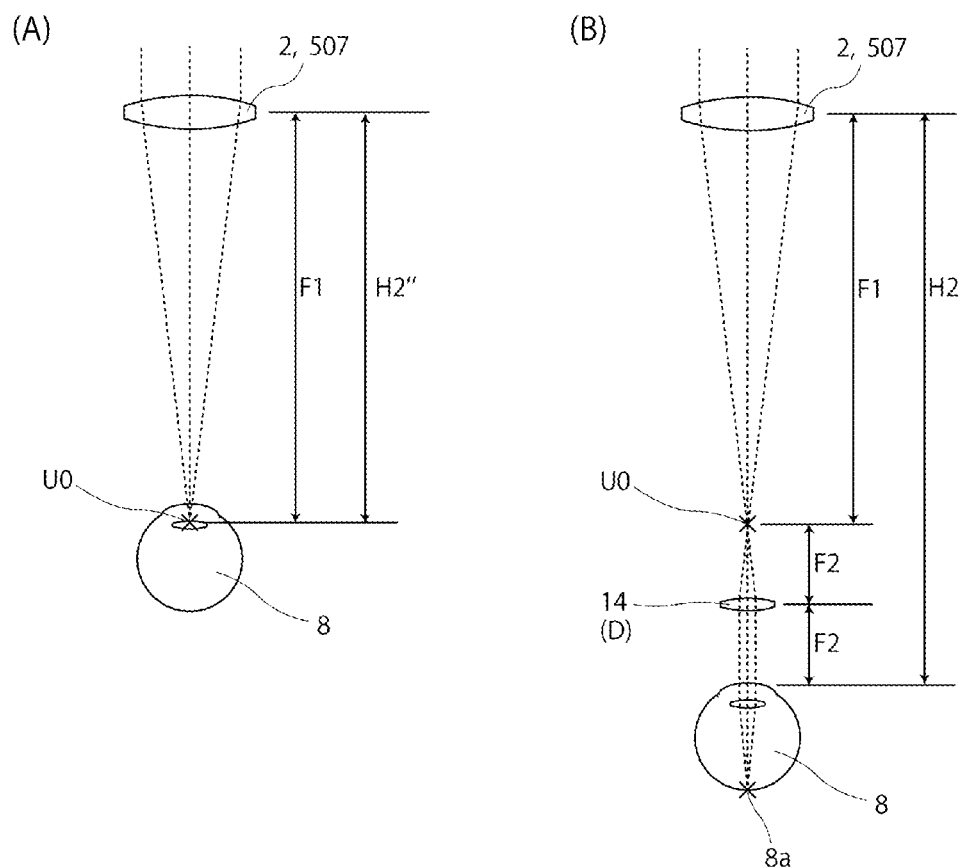
FIG. 11 is a drawing schematically illustrating a difference in optical path length between a case where a front lens is inserted on an optical path between an objective lens and a subject eye and a case where the front lens is released, in the microscope of the first embodiment of the present invention.

FIG. 11 is a schematic view illustrating, by comparison, a difference in optical path length between a case where the front lens is inserted on the optical path between the objective lens and the subject eye and a case where the front lens is released. FIG. 11(A) illustrates a case in which an anterior ocular segment, such as the cornea or iris, is observed without inserting the front lens between the objective lens and the subject eye, and FIG. 11(B) illustrates a case in which a posterior ocular segment, such as the retina of the fundus oculi, is observed by inserting the front lens between the objective lens and the subject eye.

As is clear from the comparison between FIG. 11(A) and FIG. 11(B), the optical path length of measurement light of the OCT optical system is longer in the case of FIG. 11(B) in which the posterior ocular segment is observed by inserting the front lens on the optical path between the objective lens and the subject eye, than in the case of FIG. 11(A) in which the anterior ocular segment is observed without inserting the front lens. The difference is, in the optical path length in one-side direction, F2 (focal distance of front lens)×2+eye axis length (distance from apex of cornea to fundus oculi).

As described above, in the OCT, when measurement light and reference light are caused to interfere with each other, it is necessary to make the measurement light and reference light travel over the same distance, and it is thus necessary to make the optical path length of the measurement light equal to the optical path length of the reference light. Therefore, if the optical path length of the measurement light increases by the insertion of the front lens on the optical path, it is necessary to increase the optical path length of the reference light accordingly.

In the microscope of the first embodiment, in interlock with the insertion/release of the front lens on/from the optical path, the corner cube 1010 in the OCT unit illustrated in FIG. 7 is moved, and thereby the length of the optical path of reference light can automatically be increased by a fixed value.

As described above, compared to the case of FIG. 11(A) in which the front lens is not inserted on the optical path, in the case of FIG. 11(B) in which the front lens is inserted on the optical path, the optical path length of measurement light becomes longer by "F2×2+eye axis length" in the optical path length in one-side direction. Accordingly, by automatically moving the reference position of the corner cube 1010 illustrated in FIG. 7 by "F2×2+eye axis length" in interlock with the insertion of the front lens, the length of the optical path of reference light can be increased by "F2×2+eye axis length" in the optical path length in one-side direction. Here, as the "eye axis length", an average eye axis length of humans is used. However, since the eye axis length varies from individual to individual, the optical path length of reference light can finely be adjusted in the microscope of the first embodiment.

3. Control Mechanism

It is preferable that the microscope of the present invention includes a) a lens discrimination mechanism which acquires information relating to the focal distance of the front lens that is inserted on the optical path between the subject eye and the objective lens, b) a position adjusting mechanism which adjusts the distance between the objective lens and the front lens and/or the distance between the OCT objective lens and the front lens, and c) a control mechanism which controls the position adjusting mechanism, based on the information which relates to the focal distance of the front lens and is acquired by the lens discrimination mechanism.

The "information relating to the focal distance" means not only the value itself of the focal distance of the front lens, but also any kind of information corresponding to the focal distance of the front lens. For example, although not limited to the following, the "information relating to the focal distance" may be a value relating to the power (refracting power) of the front lens, which is an inverse number of the focal distance, or ID information of the front lens.

In addition, the (a) lens discrimination mechanism may be any kind of mechanism if the mechanism can acquire information relating to the focal distance of the front lens that is inserted on the optical path, and can send the information to the control mechanism. For example, although not limited to the following, the (a) lens discrimination mechanism may be a mechanism which acquires the value of the focal distance of the front lens by a tag reader, with a tag including the value of the focal distance being attached to the front lens, and sends the acquired value to the control mechanism. Besides, the (a) lens discrimination mechanism may be implemented in such a mode that an ID tag is attached to the front lens and the ID information of the front lens is acquired by the tag reader. In this case, the control mechanism acquires the ID information of the front lens, accesses the information of a storage medium, and acquires the value of the focal distance of the ID of the front lens, thereby being able to acquire the value of the focal distance of the front lens that is inserted on the optical path.

As the tag used here, although not limited to the following, use can be made of, for example, a wireless tag such as an RFID tag or an IC tag, a tag in which information is magnetically recorded, or a tag in which information is recorded by a bar code.

The (b) position adjusting mechanism may be any kind of mechanism if the mechanism can adjust the distance between the objective lens and the front lens and/or the distance between the OCT objective lens and the front lens. For example, although not limited to the following, the (b) position adjusting mechanism may be a mechanical mechanism which can move all of the objective lens, OCT objective lens and front lens, relative to the microscope main body, by the driving force of the actuator. Besides, the (b) position adjusting mechanism may be a mechanical mechanism which simultaneously varies both the distance to the objective lens and the distance to the OCT objective lens by moving only the front lens relative to the microscope main body by the driving force of the actuator.

The (c) control mechanism may be any kind of mechanism if the mechanism controls the position adjusting mechanism, based on the information which relates to the focal distance of the front lens and is acquired by the lens discrimination mechanism. For example, although not limited to the following, the (c) control mechanism may be an electronic circuit which calculates H1 by adding the value F1 of the focal distance of the objective lens 2 illustrated in FIG. 8 and the value F2 of the focal distance of the front lens 14, and controls the motor 2006 of the front lens position control mechanism 20 illustrated in FIG. 10, such that the distance between the objective lens 2 and front lens 14 becomes H1.

4. Shape of Objective Lens

As regards the objective lens used in the microscope of the present invention, it is preferable that the objective lens decreases the angle between the optical axis of the function expansion optical system and the optical axis of the observation optical system. For this purpose, the objective lens is formed to have a notched shape by notching a part of the objective lens, and the function expansion objective lens is disposed in the notched part. Thereby, the angle between the optical axis of the function expansion optical system and the optical axis of the observation optical system can be decreased without the optical axis of the function expansion optical system passing through the objective lens.

In the present invention, the angle between the optical axis of the function expansion optical system and the optical axis of the observation optical system (one of the optical axes of the left and right observation optical paths) is preferably set at 1 to 15°, more preferably set at 4 to 10°, and still more preferably set at 6 to 8°.

In the present invention, as the objective lens having a partly notched shape, it is preferable to use an objective lens having a partial shape of a circular lens.

Here, the "partial shape of a circular lens" means such a shape that a part of a circular lens is cut off when the lens is viewed in plan in the optical axis direction of the lens. Although not limited to the following, use can be made of, for example, a lens which is cut off in a semicircular shape, a fan shape or a rectangular shape such that the optical path of the left-eye observation optical system and the optical path of the right-eye observation optical system pass through the lens.

In the microscope of the present invention, a circular lens, or a lens composed of a part of a circular lens, may be divided into two lenses, one of the divided lenses can be used as the objective lens through which the optical axis of the observation optical system passes, and the other of the divided lenses can be used as the function expansion objective lens through which the optical axis of the function expansion optical system passes.

5. Second Embodiment

Figure 12:
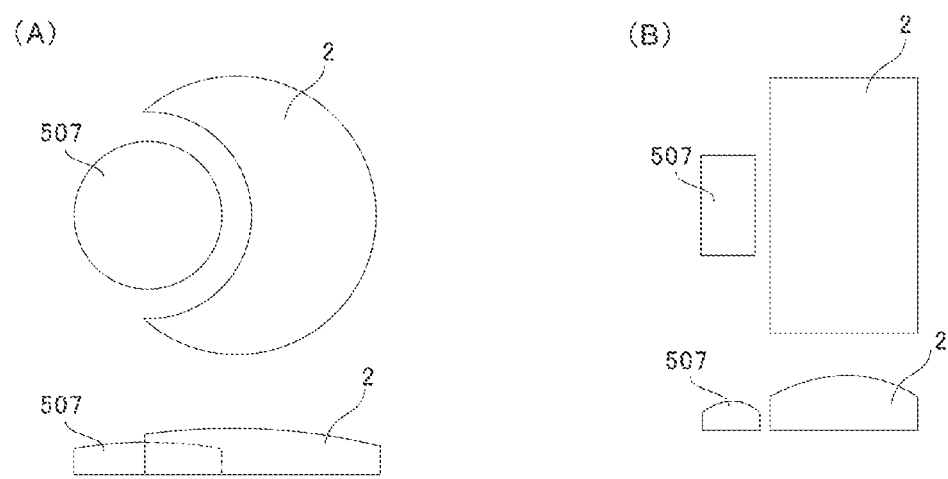
FIG. 12 is an explanatory view illustrating other concrete examples of the objective lens of the observation optical system used in a microscope of a second embodiment of the present invention.
Figure 13:
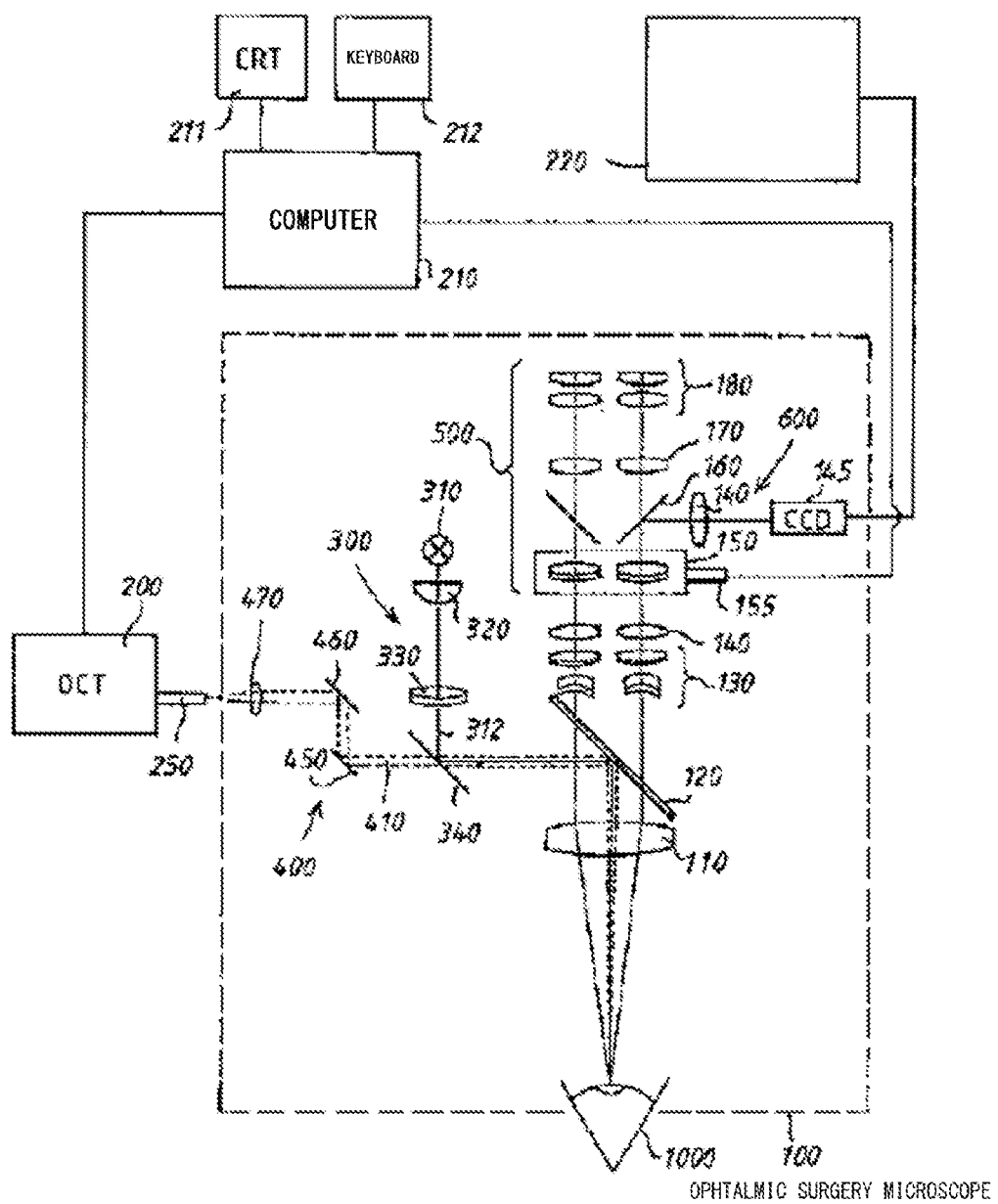
FIG. 13 is a drawing in which FIG. 1 of patent document 1 is cited.

FIG. 12 illustrates shapes of the objective lens for the observation optical system and the function expansion objective lens, which are used in a second embodiment of the microscope of the present invention. FIG. 12(A) is a view illustrating an objective lens 2 for the observation optical system, which is configured such that a circular convex lens is cut by a curved surface (a partial circle in plan-view shape) which is parallel to the optical axis, and a circular function expansion objective lens 507 (convex lens) which is disposed in the cut part. FIG. 12(B) is a view illustrating an objective lens 2 for the observation optical system with a rectangular shape in plan view, which is configured such that a circular convex lens is cut by a plane parallel to the optical axis, and a function expansion objective lens 507 (convex lens) with a rectangular shape in plan view, which is disposed in the cut part.

The embodiments of the present invention have been described above. The present invention is not limited to the above embodiments, and changes of conditions, etc., which are made without departing from the spirit of the invention, are all within the scope of the present invention.

REFERENCE SIGNS LIST

1 Microscope
2 Objective lens
5 OCT apparatus
6 Microscope main body
7 OCT function expansion unit
8 Subject eye
8a Retina
9 Illumination light source
10 OCT main body unit
12 Arithmetic control unit
13 Display unit
14 Front lens
15 Support column
16 Arm
17 X-Y fine movement apparatus
18 Surgeon microscope
19 Assistant microscope
20 Front lens position adjusting mechanism
21 Footswitch
22 Lens-barrel
23 Holding arm
24 Holding plate
25 Tag detector
26 Fixing bracket
27 Inverter unit
28 Switching lever
300 Illumination optical system
301 Optical fiber
302 Emission light diaphragm
303 Condenser lens
304 Illumination field diaphragm
305 Collimate lens
306 Reflection mirror
400 Observation optical system
400L Left-eye observation optical system
400R Right-eye observation optical system
401 Variable power lens system
402 Beam splitter
403 Imaging lens
404 Image erecting prism
405 Interpupillary distance adjusting prism
406 View field diaphragm
407 Ocular lens
500 OCT measurement light optical system
501 Optical fiber
502 Collimate lens
503 Scanning function unit
503a Galvano mirror
503b Galvano mirror
507 Function expansion objective lens, OCT objective lens
510 First optical member
511 First reflecting member
512 Second optical member
513 Second reflecting member
1001 OCT light source unit
1002 Optical fiber
1003 Polarization controller
1004 Optical fiber
1005 Fiber coupler
1006 Optical fiber
1007 Collimator
1008 Optical path length correction member
1009 Dispersion compensation member
1010 Corner cube
1011 Collimator
1012 Optical fiber
1013 Polarization controller
1014 Optical fiber
1015 Attenuator
1016 Optical fiber
1017 Fiber coupler
1018 Optical fiber
1019 Optical fiber
1020 Optical fiber
1021 Detector 1100 Photographing optical system
1101 Imaging lens
1102 Reflection mirror
1103 TV camera
2001 Support bracket
2002 Rotation screw
2003 Movable plate
2004 Coupling arm
2005 Fine movement adjusting knob
2006 Motor
F1 Focal distance of objective lens
F2, F2' Focal distance of front lens
H1, H1' Distance between objective lens and front lens
H2, H2', H2" Distance between objective lens and subject eye
L0 Light output from OCT light source unit
LC Interference light
LR Reference light
LS Measurement light
O-400 Optical axis of observation optical system
O-400L Optical axis of left-eye observation optical system
O-400R Optical axis of right-eye observation optical system
O-500 Optical axis of OCT measurement light optical system
O-501 First optical axis
O-502 Second optical axis
O-503 Third optical axis
U0 Front-side focal point position

The invention claimed is:

1. A microscope comprising, in addition to an observation optical system for observing an observation target, a function expansion optical system for radiating light from a light source onto the observation target and acquiring, from the observation target, information other than information by the observation, or for applying a process by light to the observation target,
the function expansion optical system comprising:
a first optical member configured to guide light from the light source in a first optical axis direction;
a first reflecting member configured to guide the light guided in the first optical axis direction in a second optical axis direction substantially orthogonal to the first optical axis direction;
a second optical member configured to relay the light guided in the second optical axis direction;
a second reflecting member configured to guide the light relayed by the second optical member in a third optical axis direction substantially orthogonal to the second optical axis direction; and
a function expansion objective lens disposed on the third optical axis direction and configured to radiate the light guided in the third optical axis direction onto a predetermined portion of the observation target;
wherein the first optical axis direction, the second optical axis direction, and the third optical axis direction are distinct optical axis directions;
wherein an objective lens for the observation optical system has such a shape that a part of the objective lens for the observation optical system is notched, and the function expansion objective lens is disposed in the notched part; and
whereby an optical axis of the function expansion optical system does not pass through the objective lens through which an optical axis of the observation optical system passes.

2. The microscope according to claim 1,
wherein
the light source is an OCT light source,
the function expansion optical system is an OCT optical system including an OCT measurement light optical system constituting a reciprocal light guide path of measurement light from the OCT light source, and an OCT reference light optical system constituting a light guide path of reference light from the OCT light source, and
the function expansion objective lens is an OCT objective lens.

3. The microscope according to claim 2,
wherein
the observation target is a subject eye,
the microscope includes a front lens for switching an observation position of the subject eye,
when the front lens is inserted on an optical path between the subject eye and the objective lens, the optical axis of the observation optical system and the optical axis of the OCT measurement light optical system pass through the front lens,
in accordance with a focal distance of the front lens inserted on the optical path between the subject eye and the objective lens, a distance (1) and/or a distance (2) below automatically varies,
1) The distance between the objective lens and the front lens, and
2) the distance between the OCT objective lens and the front lens, and
when the front lens is inserted and released on the optical axis between the subject eye and the objective lens, a length of an optical path of the OCT reference light optical system automatically varies in accordance with the focal distance of the front lens.

4. The microscope according to claim 3, further comprising:
a lens discrimination mechanism configured to acquire information relating to the focal distance of the front lens that is inserted on the optical path between the subject eye and the objective lens;
a position adjusting mechanism configured to adjust a distance between the objective lens and the front lens and/or a distance between the OCT objective lens and the front lens; and
a control mechanism configured to control the position adjusting mechanism, based on the information which relates to the focal distance of the front lens and is acquired by the lens discrimination mechanism.

5. The microscope according to claim 1, wherein the function expansion optical system is incorporated as an expansion unit.

6. The microscope according to claim 1,
wherein
when a microscope main body is viewed from a front side,
an optical path along the first optical axis direction is formed from a rear toward a front at a slightly outward left or right position of the microscope main body,
an optical path along the second optical axis direction is formed from an outside toward an inside of the microscope main body, and
an optical path along the third optical axis direction is formed to extend through the function expansion objective lens from above downward in a center of the microscope main body.

* * * * *